US00PP09353P

United States Patent [19]

Hanes

[11] Patent Number: Plant 9,353

[45] Date of Patent: Oct. 31, 1995

[54] IVY GERANIUM NAMED 'FREESTYLE LAVENDER'

[75] Inventor: Mitchell E. Hanes, Morgan Hill, Calif.

[73] Assignee: Goldsmith Seeds, Inc., Gilroy, Calif.

[21] Appl. No.: 364,875

[22] Filed: Dec. 27, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Henderson & Sturm

[57] ABSTRACT

A new ivy geranium cultivar particularly distinguished by mid-green foliage with light zonation, lavender color, and semi-double flowers on large umbels, fast rooting and a compact growth habit.

1 Drawing Sheet

BACKGROUND OF THE NEW PLANT

The present invention comprises a new and distinct cultivar of geranium, botanically known as *Pelargonium peltatum,* and hereinafter referred to by the cultivar name Freestyle Lavender. The new cultivar is propagated from a seedling resulting from the cross of a seed parent 2940-1 and the pollen parent, an ivy geranium known as Amethyst (not a patented variety).

Freestyle Lavender is a product of a planned breeding program intended to create new ivy geranium cultivars with lavender colored flowers, semi-double flower form, mid-green foliage, vigorous growth and superior cutting productivity.

The new cultivar was created in 1992 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
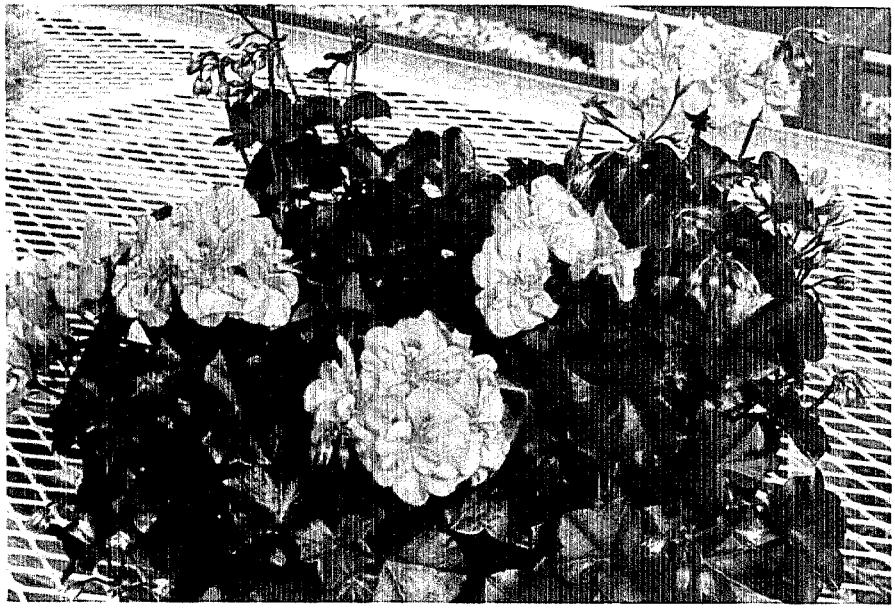
FIG. 1 shows overall plant habit.
Figure 2:
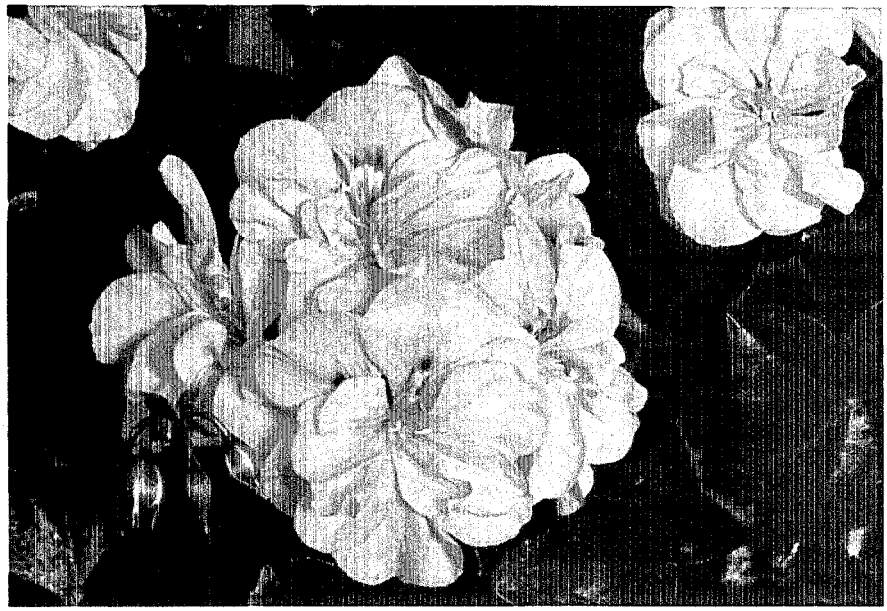
FIG. 2 illustrates the mature flower.

The following detailed descriptions set forth the distinctive characteristics of Freestyle Lavender. The data which defines these characteristics were collected from asexual reproductions carried out by Goldsmith Seeds, Inc. in Gilroy, Calif. The plant history was taken on 21 week old plants, blossomed under natural light in a greenhouse and color readings were taken in the greenhouse (in Gilroy, Calif.) on Nov. 8, 1994 under ambient light. Color references are primarily to the RHS Colour Chart of the Royal Horticultural Society of London (RHS).

THE PLANT

Classification:

*Botanical.*—*Pelargonium peltatum.*

*Commercial.*—Ivy geranium.

Form: Compact free branching.

Height: 12–15 cm, as a 6 inch pot plant, excluding blooms.

Growth: Rounded growth habit with short internodes.

Strength: Mid-green shiny foliage on a plant that has some resistance to edema. Good shipping ability as rooted or unrooted cuttings.

Foliage: Abundant quantity.

*Leaves.*—Size: Diameter about 6.5 cm. Shape: Ivy-shaped leaf with edges raised above the plane of the center of the leaf. Margin: Smooth. Texture: Waxy on both surfaces. Ribs: Radiate from the point of attachment of the petiole. Veins: Present but very inconspicuous. Color: Upper side: Darker green with a ring shaped zone circling the center of the leaf. Under side: Lighter green color without zonation. Veins a little more distinct than on the upper leaf surface. Petioles: About 3.5–5.0 cm in length on a mature leaf.

THE BUD

Size:

*Diameter.*—About 7 mm.

*Length.*—About 1.4–2.0 cm at time of bud opening.

Shape: Pointed ovoid.

Sepals: 5 in number, flat behind petals. Pointed linear lanceolate, 144A RHS in an open flower.

THE FLOWER

Blooming habit: Continuous throughout the year.

Size: Approximately 5.5 cm diameter, 1.8 cm deep.

Form: Semi-double.

Petals: About 8 outer petals, 1.8–2.2 cm wide and approximately 2.7 cm long. Approximately six inner smaller petaloids of varying shape. Both the outer petals and inner petaloids are 80B-C RHS from the base of the petal to the outer margin. The two top petals have a feather vein pattern that is 61A RHS color. Veins slightly darker than interveinal regions. Color changing little with age. Underside of petals lighter. Petals and petaloids soft and satiny.

Pedicel: Approximately 2.5 cm in length.

Persistence: Non-shattering flower.

INFLORESCENCE

Type: An umbel composed of about 8–10 flowers, erect or laterally ascending.

Peduncle: Approximately 7–8.5 cm in length, green without pigmentation.

REPRODUCTIVE ORGANS

Stamens:

*Anthers.*—7–8 positioned below the mature stigma, dull red prior to anthesis.

*Filaments.*—White near base and mid length, graduating to dull red near anther.

*Pollen.*—Orange in color.

Pistil:

*Number.*—1.

*Length.*—Approximately 11 mm.

*Stigma.*—5 linear lobes of near equal length, curling back toward ovary, purplish-red.

*Style.*—Length: About 6 mm. Color: Purplish red.

*Ovaries.*—At anthesis, densely pubescent with white hairs, oblong. Green drying to a light brown at maturity.

*Fruit.*—Partially fertile.

I claim:

1. A new and distinct cultivar of ivy geranium substantially as herein shown and described, named Freestyle Lavender, that is characterized by: mid-green foliage with light zonation, lavender color, and semi-double flowers on large umbels, fast rooting and a compact growth habit.

* * * * *